United States Patent [19]
Hack et al.

[11] Patent Number: 5,874,066
[45] Date of Patent: Feb. 23, 1999

[54] METHOD AND KIT FOR TREATING TOOTH HYPERSENSITIVITY

[75] Inventors: Gary David Hack, Columbia; Van Purdy Thompson, Riva; Joseph Anthony von Fraunhofer, Baltimore, all of Md.

[73] Assignee: University of Maryland, Baltimore, Baltimore, Md.

[21] Appl. No.: 901,083

[22] Filed: Jul. 28, 1997

Related U.S. Application Data

[63] Continuation of Ser. No. 282,960, Aug. 1, 1994, abandoned.
[51] Int. Cl.$^6$ .............................. A61K 6/02; A61K 7/16
[52] U.S. Cl. ..................... 424/49; 433/215; 433/228.1; 106/35
[58] Field of Search ..................... 106/35; 424/49–58; 433/215, 228.1

[56] References Cited

U.S. PATENT DOCUMENTS

| | | |
|---|---|---|
| 4,057,621 | 11/1977 | Pashley et al. . |
| 4,080,440 | 3/1978 | DiGiulio et al. ........................ 424/49 |
| 4,538,990 | 9/1985 | Pashley . |
| 4,772,573 | 9/1988 | Toriyama et al. . |
| 4,952,613 | 8/1990 | Hosada .................................. 523/109 |
| 5,026,539 | 6/1991 | Jackson et al. . |
| 5,037,639 | 8/1991 | Tung, I .................................. 424/57 |
| 5,234,971 | 8/1993 | Imai et al. ............................. 523/113 |
| 5,268,167 | 12/1993 | Tung, II ................................ 424/52 |
| 5,270,031 | 12/1993 | Lim et al. .............................. 424/49 |
| 5,330,746 | 7/1994 | Friedman et al. ..................... 424/49 |

OTHER PUBLICATIONS

Knight et al., "Hypersensitive Dentin: Testing of Procedures for Mechanical and Clinical Obliteration of Dentinal Tubuli", J. Periodontal 64:5, pp. 366–373 (May, 1993).

Markowitz et al, "Hypersensitive Teeth: Experimental Studies of Dentinal Desensitizing Agents", *Dental Clinics of America*, 34(3):491–501 (1990).

Kim, "Hypersensitive Teeth: Densensitization of Pulpal Sensory Nerves", *J. of Endodontics*, 12(10):482–485 (1986).

Manochehr et al, "Clinical Evaluation of Two Potassium Nitrate Toothpaste for the Treatment of Dental Hypersensitivity", *Peridontal Case Reports*, 6(1):25–30 (1984).

Gortner, Jr. et al, "Some Effects of Dietary Oxalate on the Teeth of White Rats", *J. of Nutrition*, 32:121–131 (1946).

Kaminske et al, "Effects of Oxalate and Calcium Phosphate Solutions on Dentin Tubule Obstruction", *J. of Dental Res.*, Abstract 480, p. 168 (Mar. 7–11, 1990).

Pashley et al, "Treatment of Dentin Sensitivity Through Tubule Occlusion", *J. Dental Res.*, Abstract S46, p. 100 (Mar. 11–15, 1987).

Markowitz et al, "Decreasing Intradental Nerve Activity in the Cat with Potassium and Divalent Cations", *Archs. Oral Biol.*, 36(1):1–7 (1991).

Minkoff et al, "Efficacy of Strontium Chloride in Dental Hypersensitivity", *J. Peridontal.*, 58(7):470–474 (1987).

Uchida et al, "Controlled Clinical Evaluation of a 10% Strontium Chloride Dentifice in Treatment of Dentin Hypersensitivity Following Periodontal Surgery", *J. Peridontal.*, 51(10):578–581 (1980).

Hodosh, "A Superior Desensitizer—Potassium Nitrate", *JADA*, 88:831–832 (1974).

Hirvonen et al, "The Excitability of Dog Pulp Nerves in Relation to the Condition of Dentine Surface", *J. Endodontics*, 10(7):294–298 (1984).

Greenhill et al, "The Effects of Densensitizing Agents on the Hydraulic Conductance of Human Dentin In Vitro", *J. Dent. Res.*, 60(3):686–698 (1981).

Pashley et al, "Dentin Permeability: Effects of Desensitizing Dentifrices In Vitro", *J. Peridontal.*, 55(9):522–525 (1984).

Muzzin et al, "Effects of Potassium Oxalate on Dentin Hypersensitivity In Vitro", *J. Peridontol.*, 60(3):151–158 (1989).

Imai et al, "A New Treatment for Dentin Hypersensitivity by Precipitation of Calcium Phosphate In Situ", *Dental Materials Journal*, 9(2): 167–172 (1990).

Pashley et al, "The Effects of Oxalate Treatment on the Smear Layer of Ground Surfaces of Human Dentine", *Archs. Oral Biol.*, 30(10):731–737 (1985).

Kanapka, "Tooth Hypersensitivity: Over–the–Counter Dentifrices in the Treatment of Tooth Hypersensitivity", *Dental Clinics of North America*, 34(4):545–560 (1990).

Pashley et al, "The Effect of Molecular Size on Reflection Coefficients in Human Dentine", *Archs. Oral Biol.*, 24:455–460 (1979).

Pashley et al, "Effects on the Degree of Tubule Occlusion on the Permeability of Human Dentine In Vitro", *Archs. Oral Biol.*, 23:1127–1133 (1978).

Trowbridge et al, "Tooth Hypersensitivity: A Review of Current Approaches to In–Office Management of Tooth Hypersensitivity", *Dental Clinics of North America*, 34(3):561–581 (1990).

Rosenthal, "Historic Review of the Management of Tooth Hypersensitivity", *Dental Clinics of North America*, 34(3):403–427 (1990).

*Primary Examiner*—Shep K. Rose
*Attorney, Agent, or Firm*—Chalin A. Smith; Office of Research & Development

[57] ABSTRACT

A two-step method for treating tooth hypersensitivity so as to prevent, reduce or eliminate the same, and a kit for use in the same, are disclosed.

20 Claims, No Drawings

METHOD AND KIT FOR TREATING TOOTH HYPERSENSITIVITY

This is a Continuation of Application Ser. No. 08/282,960 filed 1 Aug. 1994.

FIELD OF THE INVENTION

The present invention relates to a two-step method for treating tooth hypersensitivity so as to prevent, reduce or eliminate the same, and a kit for use in the same.

BACKGROUND OF THE INVENTION

Tooth hypersensitivity is a common problem which affects about 40 million adults in the United States, 10 million of which can be considered chronically affected (Kanapka, *Dent. Clin. North Am.*, 34:54 (1990)). It is estimated that some 14% of adults in the U.S. have at least one or more sensitive teeth. The teeth may be sensitive to cold, heat, air or sugary foods.

The incidence of tooth hypersensitivity increases with age. The increased incidence is believed to be related to the general increase in exposed root surfaces of teeth as a result of periodontal disease, tooth brush abrasion or cyclic loading fatigue of the thin enamel near the dento-enamel junction.

The currently accepted theory for tooth hypersensitivity is called the hydrodynamic theory. This theory is based on the belief that open dentinal tubules allow fluid flow through the tubules. This flow excites the nerve endings in the dental pulp. Clinical replicas of sensitive teeth viewed in the scanning electron microscope (SEM) reveal varying numbers of open or partially open dentinal tubules.

Tubules generally are not seen at the tooth root surface because of the cementum covering the tooth root, or because of a smear layer of dentinal debris 2–5 microns in thickness that covers the tooth surface and masks the tubules. When the smear layer is present on the dentin, the fluid flow that can occur through the dentin is only a few percent of that possible following acid removal of the smear layer, which "opens" or uncovers the tubules.

There is a growing body of evidence that occlusion of the dentinal tubules of a sensitive tooth, whether by resin infiltration, varnish coat or more recently by crystallite precipitation, results in reduction or elimination of the hypersensitivity. The duration of relief, however, is highly variable. Hypersensitivity usually reappears because of tooth brush abrasion, presence of acid challenges in the mouth or aging of the coating material.

Various agents have been used to reduce tooth hypersensitivity, including potassium nitrate (Hodosh, *J. Am. Dent. Assoc.*, 88:831 (1974), which is the active ingredient in the dentifrice AQUAFRESH SENSITIVE™; strontium chloride, which is the active ingredient in the dentifrice SENSODYNE™; and other reagents, such as sodium fluoride, which dentists may apply directly to the dentin to reduce sensitivity.

A two-step procedure involving application of a calcium nitrate solution and a potassium phosphate solution to the tooth has been found to produce numerous calcium phosphate crystals (Kaminske et al, *J. Dent. Res.*, 69:68 (1990)).

Increasing concentrations of oxalic acid in the food bolus derived from dietary sources, up to 1.14 g/l, have also been found to yield precipitation of a deposit at the tooth surface. A maximal response was found to be obtained at a level of 0.1% (w/v) oxalic acid equivalents. Greater levels of oxalic acid did not yield greater protection of teeth. It has been postulated that the deposited material is calcium oxalate, resulting from interaction of the oxalic acid with calcium in the saliva (Gortner et al, *J. Nutr.*, 32:121 (1946)). However, it is well-known that the level of calcium in saliva is very low, and thus the proposed mechanism may be incorrect.

Solutions of alkali metal or ammonium oxalates have also been used to reduce tooth hypersensitivity. The low pH of these solutions is believed to mobilize calcium and phosphate from the hard tissues (U.S. Pat. No. 4,057,621).

In addition, a 3.0% (w/v) monohydrogen monopotassium oxalate solution has been found to occlude dentinal tubules (Pashley et al, *Arch. Oral. Biol.*, 23:1127 (1978)).

A variety of protein precipitants and tubule occluding agents have been evaluated by measuring the effect thereof on hydraulic conductance of human dentin. Potassium oxalate has been reported to yield a large reduction in conductance (Greenhill et al, *J. Dent. Res.*, 60:686 (1981)).

Over-the-counter desensitizing dentifrices and an experimental 2.0% (w/v) potassium oxalate dentifrice for tubule occlusion have been found to be superior to the other known formulations (Pashley et al, *J. Periodont.*, 55:522 (1984)). Potassium oxalate is thought to react with the smear layer, and is believed to reduce the permeability thereof, as well as increase resistance of the layer to acid attack. It is believed that the crystals produced when employing potassium oxalate are calcium oxalate crystals (Pashley et al, *Arch. Oral Biol.*, 30:731 (1985)).

A two-component kit comprising a 1.0–30% (w/v) neutral oxalate solution, such as dipotassium oxalate, and a 0.5–3.0% (w/v) acidic oxalate solution, such as monopotassium-monohydrogen oxalate, has been described. It is asserted that the neutral oxalate forms large crystals all over the dentinal surface, and the acidic oxalate forms smaller crystals around and about the previously formed larger crystals, so as to form a combined uniform layer of microscopic crystals (U.S. Pat. No. 4,538,990).

The benefits of two potassium oxalate formulations, one comprising 30% (w/v) dipotassium oxalate, and the other 3.0% (w/v) monohydrogen-monopotassium oxalate have been evaluated. The results were varied, purportedly due to variations in the size and number of crystals generated by the two solutions, which in turn may depend on various factors, such as the pH of the solutions. The rate of crystal formation also was believed to be relevant. For example, the 30% (w/v) dipotassium oxalate reacts with ionized calcium in the dentinal fluid, and the acidic 3.0% (w/v) monohydrogen-monopotassium oxalate solution is reported to generate an extremely high local calcium ion concentration by etching the tooth, which results in greatly accelerated formation of abundant crystals to yield the desired reduction in hypersensitivity (Muzzin et al, *J. Periodont.*, 60:151 (1989)). However, there has been no explanation as to the source of ionized calcium within the dentinal fluid; further, no definition has been provided as to what is meant by the phrase "extremely high local calcium ion concentration". In this context, it should be noted that dissolution of dentinal hydroxyapatite by the acidic oxalate solution, which releases $Ca^{2+}$ ions, is limited by the amount of solution present on the dentin and by the pH at the dentin/solution interface. As the pH rises due to reaction between the acidic solution and the hydroxyapatite, the rate of hydroxyapatite dissolution will decrease, and there is an accompanying reduction in $Ca^{2+}$ ion release. These physicochemical considerations clearly limit the amount of crystal formation on the dentin surface.

A commercial product, PROTECT™ (J. O. Butler Co., Chicago, Ill.) that is marketed for occluding dentinal tubules, utilizes an acidic potassium oxalate solution which is applied to the tooth surface. However, PROTECT™ has limited effectiveness as it leaves many tubules open (Kaminske et al, *J. Dent. Res.*, 69:68 (1990)).

Accordingly, there has still been a need in the art to develop an effective treatment which will result is occlusion of substantially all of the tubules.

SUMMARY OF THE INVENTION

An object of the present invention is to provide a method for inducing copious crystal development on the entire tooth surface so as to achieve maximal dentinal tubule occlusion and thereby prevent, reduce and eliminate hypersensitivity.

Another object of the present invention is to utilize and generate compounds with analgesic activity at the tooth surface and within the dentinal tubules in conjunction with the crystal formation.

Still another object of the present invention is to provide a method which yields a source of neuroactive agents that can be present in the precipitated crystal layers or can constitute the deposited crystal themselves, and which leach out slowly with passage of time such that the desensitizing effect of the dentinal tubule occlusion is reinforced and enhanced by the neuroactive effect of the leached ions.

Yet another object of the present invention is to provide a kit for use in said method.

These and other objects of the present invention, which will be apparent from the detailed description of the invention provided hereinafter, have been met in one embodiment by a method for treating tooth hypersensitivity comprising:

(a) applying an exogenous inorganic salt solution to the tooth; and thereafter (b) applying an oxalate salt solution to the tooth;

wherein a reaction occurs between cations of said exogenous inorganic salt and anions of said oxalate salt so as to produce a precipitate which occludes dentinal tubules.

In another embodiment, the above-described objects of the present invention have been met by a kit for treating tooth hypersensitivity comprising:

(a) a first container means comprising an inorganic salt; and (b) a second container means comprising an oxalate salt.

DETAILED DESCRIPTION OF THE INVENTION

As discussed above, in one embodiment the present invention relates to a method for treating tooth hypersensitivity comprising:

(a) applying an exogenous inorganic salt solution to the tooth; and thereafter (b) applying an oxalate salt solution to the tooth;

wherein a reaction occurs between cations of said exogenous inorganic salt and anions of said oxalate salt so as to produce a precipitate which occludes dentinal tubules.

As used herein, the expression "solution" is intended to include an aqueous solution, a gel or a paste.

Step (a) in said method involves applying an exogenous inorganic salt to the tooth surface. The expression "exogenous" herein refers to a solution which is not naturally present in the mouth through either the chemical nature or the concentration of its constituents. Saliva, which contains many different cations and anions, is a naturally-occurring chloride-containing solution that also contains sodium, calcium and phosphate ions in an amount of about 0.1% (w/v) or less. As used herein, a 1.0% (w/v) solution of calcium chloride would be an "exogenous" solution because the level of $Ca^{2+}$ therein is higher than that occurring naturally in saliva.

The particular inorganic salt employed in the present invention is not critical thereto. Examples of said inorganic salts include chlorides, fluorides, iodides and nitrates of calcium, strontium, sodium, iron ($Fe^{III}$) and potassium, alone or in combination. of these, strontium and potassium chlorides and nitrates are preferred since their cations are known to be neuroactive agents.

The concentration range of the exogenous inorganic salt in the solution is generally from about 1.0% (w/v) to 20% (w/v), preferably about 1.0% (w/v) to 15% (w/v), more preferably about 10% (w/v). The inorganic salt is typically dissolved in an aqueous medium, preferably water.

The pH of the inorganic salt solution is generally adjusted to be in the range of about 1 to 11, preferably about pH 1 to 8. This adjustment can be achieved, as appropriate, by the addition of hydrochloric, sulfuric, nitric, acetic, citric acid or other acid, or with sodium, potassium, ammonium or calcium hydroxide or any other suitable base.

Use of neutral or basic inorganic salt solutions is beneficial, as there is a tendency for acidic solutions to remove the smear layer. That is, it is known that basic solutions advantageously tend to remove adherent polysaccharide coatings from the dentin surface, thereby enhancing access to the dentinal tubules. Accordingly, in one embodiment, the present invention provides benefits over currently used acidic treatments which have a greater tendency to etch the tooth surface.

Step (b) in said method involves applying an oxalate salt to the tooth surface which has been pre-treated with the inorganic salt solution. Oxalate is not normally present at appreciable concentrations in the mouth.

The particular oxalate salt is not critical to the present invention. Examples of said oxalate salt include monopotassium hydrogen oxalate, monosodium hydrogen oxalate, dipotassium oxalate, disodium oxalate, diammonium oxalate, ammonium acid oxalate, aluminum oxalate and ferric oxalate, alone or in combination. Monopotassium hydrogen oxalate, monosodium hydrogen oxalate, dipotassium oxalate and disodium oxalate are the preferred oxalate salts. These salts are preferred because in the presence of the inorganic salt solution a continuous crystalline layer clearly forms on the tooth surface.

The concentration range of the oxalate salt in the solution is generally from about 1.0% (w/v) to 15% (w/v), preferably about 1.0% (w/v) to 10% (w/v), more preferably about 1.0 (w/v) to 5.0% (w/v), most preferably about 3.0% (w/v). The oxalate salt is typically dissolved in an aqueous medium, preferably water.

The pH of oxalate salt solution is generally adjusted to be in the range of about 1 to 11, preferably about 1 to 8. This adjustment can be achieved, as appropriate, by the addition of hydrochloric, sulfuric, nitric, acetic, citric or any other acid, or with sodium, ammonium, potassium or calcium hydroxide or any other suitable base.

Specific examples of combinations of the salt solutions which can be used in the present invention include:

i. chloride or nitrate salts of calcium or strontium at a concentration of 10% (w/v) (pH 4–8), or combinations thereof used with;

ii. a 3.0% (w/v) solution of potassium, sodium, ammonium, aluminum or ferric acid oxalate (monohydrogen oxalate) (pH 2–7); or a 3.0% (w/v) solution of dipotassium, disodium or diammonium oxalate (pH 2–7).

In the above method, calcium ions derived from the tooth surface may also react with the oxalate salt solution so as to aid in the production of a precipitate which occludes dentinal tubules.

The inorganic salt or oxalate salt solutions can also contain a viscosity-modifying agent so as to form a gel or a paste. Typically, fumed silica (approximate particle size of 0.04 μm) is used for gel formation. Typically, diatomaceous earth, kieselguhr and similar unreactive inert fillers are used as paste formers. These viscosity-control agents, e.g. fumed silica, may also function as crystal nucleation initiators to facilitate crystal formation. Also, to a limited extent, fumed silica absorbs to the dentin surface and can occlude dental tubules.

Generally, the concentration of said viscosity control and/or crystal nucleation initiators in each of the inorganic salt and oxalate salt solutions will be in the range of about 0.5% (w/v) to 10% (w/v), preferable about 5.0% (w/v).

In the method of the present invention, a crystalline coating is formed on the tooth surface. A unique aspect of the present invention is the optional use of non-acidic solutions. The present invention nevertheless enables use of an acidic solution, typically the oxalate salt solution is acidic. In this case, the presence of the neutral or basic inorganic salt solution at the tooth surface enables crystal formation on contact with the oxalate salt solution without tooth etching.

Also, as discussed above, some of the component solutions are simultaneously capable of reducing hypersensitivity by an analgesic effect. Unique to the combination of solutions of the present invention are possible reaction by-products, such as the chlorides and nitrates of strontium and potassium, which in and of themselves are known to decrease nerve activity and, therefore, dental hypersensitivity.

Neuroactive agents may be present in the precipitated crystal layers or may constitute the deposited crystal themselves, and may leach out slowly with passage of time such that the desensitizing effect of the dentinal tubule occlusion is reinforced and enhanced by the neuroactive effect of the leached ions. Such an effect can occur with strontium oxalate crystalline deposits which releases $Sr^{2+}$ ions through slow, continuous and progressive dissolution such that the strontium oxalate deposit will function as a "therapeutic crystal".

The solutions are applied to the tooth surface sequentially. The inorganic salt solution is applied to the tooth for at least 5 sec, preferably 10 to 60 sec, before said oxalate salt solution is applied to the tooth. It is preferred that the solutions be allowed to reside on the tooth surface for a brief period of time, e.g., for at least about 5 sec, preferably about 30 to 60 sec, although longer periods of time, e.g., up to 5 min is acceptable.

The solutions can be applied with any suitable application means, such as a cotton swab or similar applicator type device. Alternatively, as discussed above, the solutions can be applied in the form of a gel or paste.

As discussed above, in a second embodiment, the above-described objects of the present invention have been met by a kit for treating tooth hypersensitivity comprising:

(a) a first container means comprising an inorganic salt; and (b) a second container means comprising an oxalate salt.

For example, the kit can comprise two vials each separately comprising the inorganic salt and the oxalate salt, respectively. The salts can be provided in solid form in a pre-measured amount for reconstitution with an appropriate aqueous medium to obtain the preferred concentrations, or can be provided as a aqueous concentrate for appropriate dilution with a suitable aqueous medium to obtain the preferred concentrations or can be provided as solutions at the preferred concentrations.

The following examples are provided for illustrative purposes only, and are in no way intended to limit the scope of the present invention.

EXAMPLE 1

Preparation of Dentin Discs

Slices of dentin approximately 1.0–2.0 mm thick were cut from extracted teeth that had been stored in distilled water. All of the slices were cut perpendicular to the dentin tubules for uniformity, and to maximize the number of open tubules. Dentin disks were then prepared by polishing the slices through successive grades of silicon carbide abrasive paper up to 600 grit paper under running water. Thereafter, the dentin discs were rinsed for at least 30 sec in running distilled water to remove any abrasive particles from surface polishing (Sample A), or were etched for 30 sec with 37% (v/v) phosphoric acid, followed by at least a 30 sec rinse in running distilled water to remove any smear layers resulting from cutting or polishing (Sample B).

EXAMPLE 2

Treatment of Dentin Discs

A 10% (w/v) $CaCl_2$ solution (pH 6.0) was applied to the dentin discs (both Sample A and Sample B) obtained in Example 1 using a cotton pledget for approximately 2 min. Thereafter, a 3.0% (w/v) monopotassium hydrogen oxalate solution (pH 2.0) was applied in the same manner, the discs were rinsed under running distilled water for 30 sec, air dried, and prepared for SEM analysis.

For comparison, a second set of the dentin discs (both Sample A and Sample B) obtained in Example 1 were treated with a 5.0% (w/v) dipotassium oxalate solution (pH 9.0) using a cotton pledget for approximately 2 min. Next, the discs were rinsed under running distilled water for 30 sec, air dried, and prepared for SEM analysis.

Also for comparison, PROTECT™, i.e., a 3.0% (w/v) monopotassium hydrogen oxalate solution (pH 2.0), was applied to the dentin discs (both Sample A and Sample B) obtained in Example 1 for 2 min actively with a cotton pledget according to the manufacturer's instructions. Next, the discs were rinsed under running distilled water for 30 sec, air dried, and prepared for SEM analysis.

The results of the SEM analysis for dentin either left with the 600 grit smear layer (Sample A), or etched with 37% (v/v) phosphoric acid to remove the smear layer (Sample B), and subsequently treated with the 10% (w/v) $CaCl_2$ solution (pH 6.0), and then with 3.0% (w/v) monopotassium hydrogen oxalate solution (pH 2.0) showed copious surface crystal formation. On the other hand, only a relatively few calcium oxalate crystals were formed when the dentin discs (both Sample A and Sample B) were treated with only the 5.0% (w/v) dipotassium oxalate solution (pH 9.0), or with only the commercially available 3.0% (w/v) monopotassium hydrogen oxalate (pH 2.0). It was estimated that the crystal formation seen using the two-step method of the present invention was at least 10–100 times greater than that seen using the above-described comparative one-step methods. In addition, SEM analysis revealed that the number of occluded tubules obtained using PROTECT™ and the 5.0% (w/v) dipotassium oxalate solution (pH 9.0) was about 1–5% of the number observed to be occluded using the two-step method of the present invention.

EXAMPLE 3

Clinical Trial 120 adult patients were selected at random for inclusion in a clinical trial. All 120 patients exhibited dentinal hypersensitivity. The 120 patients were divided randomly into 4 groups of 30 patients each. A team of dentists performed all aspects of the clinical trial. The patients were tested for sensitivity to cold and tactile stimulation when first presenting to the examining dentist. Each group of patients were then treated with only one of the following regimens:

(a) the commercial product PROTECT™;

(b) an initial 10% (w/v) calcium chloride solution (pH 6.0) treatment, followed by a 5.0% (w/v) dipotassium oxalate solution (pH 9.0) treatment about 10 sec later (c) an initial 10% (w/v) sodium chloride solution (pH 6.0) treatment, followed by a 5.0% (w/v) dipotassium oxalate solution (pH 9.0) treatment about 10 sec later; or (d) by a 5.0% (w/v) dipotassium oxalate solution (pH 9.0).

After the treatment, the patients were retested for sensitivity to cold and tactile stimulation by the examining dentist. It was thus found, that patients treated with the two-step method employing calcium chloride and dipotassium oxalate, as well as the two-step method employing sodium chloride and dipotassium oxalate, exhibited significantly less hypersensitivity than patients treated with the one-step method employing the potassium oxalate solution (PROTECT™) or the dipotassium oxalate solution.

While the invention has been described in detail and with reference to specific embodiments thereof, it will be apparent to one skilled in the art that various changes and modifications can be made therein without departing from the spirit and scope thereof.

What is claimed is:

1. A method for treating dentinal hypersensitivity consisting essentially of:

(a) applying to an exposed dentin surface a first solution consisting essentially of a calcium or strontium salt of a chloride or nitrate at a concentration of about 1.0% (w/v) to about 20.0% (w/v) at a pH of about 1 to about 11; and thereafter (b) applying to said exposed dentin surface a second solution consisting essentially of potassium oxalate at a concentration of about 1.0% (w/v) to about 7.0% (w/v) at a pH of about 2 to about 6;

(c) incubating the two solutions for a time sufficient for a precipitate of dentinal tubule occluding oxalate crystals of strontium or calcium to be deposited both upon said exposed dentinal surface and within the dentinal tubules of said exposed dentin, while simultaneously forming a neuroactive amount of potassium salt of nitrate or chloride, said potassium salt being held in close proximity to the dentinal tubules by said oxalate crystals; and (d) washing said solutions from said exposed dentinal surface without removing said precipitate from said tooth.

2. The method of claim 1, wherein said concentration of said first solution is about 1.0% (w/v) to about 15% (w/v).

3. The method of claim 2, wherein said concentration is about 10% (w/v).

4. The method of claim 1, wherein said first solution has a pH of about 1 to about 8.

5. The method of claim 1, wherein said oxalate is selected from the group consisting of monopotassium hydrogen oxalate, dipotassium oxalate and a combination thereof.

6. The method of claim 1, wherein said concentration is about 1.0% (w/v) to 5.0% (w/v).

7. The method of claim 6, wherein said concentration is about 3.0% (w/v).

8. The method of claim 1, wherein said first solution is applied to the tooth at least 5 sec before said second solution is applied to the tooth.

9. The method of claim 8, wherein said first solution is applied to the tooth 10 to 60 sec before said second solution is applied to the tooth.

10. A kit for treating dentinal hypersensitivity due to the existence of exposed dentin surfaces consisting essentially of:

(a) a first container means consisting essentially of a first solution consisting essentially of a calcium or strontium salt of a chloride or nitrate at a concentration of about 1.0% (w/v) to about 20.0% (w/v) at a pH of about 1 to about 11; and (b) a second container means consisting essentially of a second solution consisting essentially of a potassium oxalate at a concentration of about 1.0% (w/v) to about 7.0% (w/v) at a pH of about 2 to about 6, wherein said solutions when mixed together simultaneously form both a precipitate of dentinal tubule occluding oxalate crystals of calcium or strontium and a neuroactive amount of a potassium salt of chloride or nitrate.

11. The kit of claim 10, wherein said oxalate is selected from the group consisting of monopotassium hydrogen oxalate, dipotassium oxalate and a combination thereof.

12. The method of claim 1, wherein said first solution contains a strontium salt.

13. The kit of claim 10, wherein said first solution contains a strontium salt.

14. The kit of claim 10, further comprising:

(c) a means for applying said solutions to a tooth.

15. A method for treating dentinal hypersensitivity consisting essentially of:

(a) applying to an exposed dentin surface a first solution consisting essentially of a calcium salt of chloride or nitrate at a concentration of about 1.0% (w/v) to about 20.0% (w/v) at a pH of about 1 to about 11; and thereafter (b) applying to said exposed dentin surface a second solution consisting essentially of a potassium oxalate, a neuroactive agent, at a concentration of about 1.0% (w/v) to about 7.0% (w/v) at a pH of about 1 to about 5;

(c) incubating the two solutions for a time sufficient for a precipitate of dentinal tubule occluding calcium oxalate crystals to be deposited both upon said exposed dentinal surface and within the dentinal tubules of said exposed dentin, while simultaneously forming a neuroactive amount of potassium salt of nitrate or chloride, said potassium salt being held in close proximity to the dentinal tubules by said oxalate crystals; and (d) washing said solutions from said tooth without removing said precipitate from said tooth.

16. A method of claim 15 wherein said first solution has a pH of about 1 to about 8.

17. A method of claim 15 wherein said second solution has a pH of about 2 to about 3.

18. A method of claim 1 wherein said first solution consists essentially of a calcium salt.

19. A method of claim 18 wherein said first solution consists essentially of a calcium chloride.

20. A method of claim 15 wherein said first solution consists essentially of a calcium chloride.

* * * * *